US009336482B1

(12) United States Patent
Corrado et al.

(10) Patent No.: US 9,336,482 B1
(45) Date of Patent: May 10, 2016

(54) PREDICTING LIKELIHOODS OF CONDITIONS BEING SATISFIED USING RECURRENT NEURAL NETWORKS

(71) Applicant: Google Inc., Mountain View, CA (US)

(72) Inventors: Gregory Sean Corrado, San Francisco, CA (US); Ilya Sutskever, Mountain View, CA (US); Jeffrey Adgate Dean, Palo Alto, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/810,381

(22) Filed: Jul. 27, 2015

(51) Int. Cl.
*G06N 3/02* (2006.01)
*G06N 3/04* (2006.01)

(52) U.S. Cl.
CPC ............... *G06N 3/0472* (2013.01); *G06N 3/02* (2013.01)

(58) Field of Classification Search
None
See application file for complete search history.

(56) References Cited

U.S. PATENT DOCUMENTS

| | | |
|---|---|---|
| 5,839,438 A | 11/1998 | Graettinger et al. |
| 6,090,044 A | 7/2000 | Bishop et al. |
| 6,306,087 B1 | 10/2001 | Barnhill et al. |

OTHER PUBLICATIONS

Verstraeten, et al., Oger: Modular Learning Architectures for Large-Scale Sequential Processing, Journal of Machine Learning Research 13 (2012) 2995-2998.*
Bengio et al., "Neural probabilistic language models," in Innovations in Machine Learning, vol. 194, pp. 137-186. Springer, 2006.
Hermann and Blunsom, "Multilingual distributed representations without word alignment," In ICLR, 2014, Mar. 2014, pp. 1-9.
Mikolov et al., "Extensions of recurrent neural network language model," In ICASSP, May 2011, pp. 5528-5531.
Mikolov et al., "Recurrent neural network based language model," In INTERSPEECH, pp. 1045-1048, Sep. 2010.
Mozer, "A Focused Backpropagation Algorithm for Temporal Pattern Recognition," Complex Systems 3, 1989, pp. 349-381.
Rumelhart et al., "Learning representations by back-propagating errors," Nature, 323(6088):533-536, Oct. 1986.

* cited by examiner

*Primary Examiner* — Wilbert L Starks
(74) *Attorney, Agent, or Firm* — Fish & Richardson P.C.

(57) ABSTRACT

Methods, systems, and apparatus, including computer programs encoded on computer storage media, for predicting likelihoods of conditions being satisfied using recurrent neural networks. One of the systems is configured to process a temporal sequence comprising a respective input at each of a plurality of time steps and comprises: one or more recurrent neural network layers; one or more logistic regression nodes, wherein each of the logistic regression nodes corresponds to a respective condition from a predetermined set of conditions, and wherein each of the logistic regression nodes is configured to, for each of the plurality of time steps: receive the network internal state for the time step; and process the network internal state for the time step in accordance with current values of a set of parameters of the logistic regression node to generate a future condition score for the corresponding condition for the time step.

20 Claims, 9 Drawing Sheets

PREDICTING LIKELIHOODS OF CONDITIONS BEING SATISFIED USING RECURRENT NEURAL NETWORKS

BACKGROUND

This specification relates to processing temporal sequences using recurrent neural networks.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

Some neural networks are recurrent neural networks. A recurrent neural network is a neural network that receives an input sequence and generates an output sequence from the input sequence. In particular, a recurrent neural network can use some or all of the internal state of the network from a previous time step in computing an output at a current time step.

SUMMARY

In general, one innovative aspect of the subject matter described in this specification can be embodied in methods for processing a temporal sequence comprising a respective input at each of a plurality of time steps using a recurrent neural network system comprising one or more recurrent neural network layers and one or more logistic regression nodes, the methods comprising the actions of, for each of the plurality of time steps: receiving the input at the time step; processing the input at the time step through the one or more recurrent neural network layers to generate a network internal state for the time step; and processing the network internal state using each of the one or more logistic regression nodes, wherein each of the logistic regression nodes corresponds to a respective condition from a predetermined set of conditions, and wherein processing the network internal state using each of the one or more logistic regression nodes comprises: processing the network internal state for the time step using the logistic regression node in accordance with current values of a set of parameters of the logistic regression node to generate a future condition score for the corresponding condition for the time step, wherein the future condition score for the corresponding condition represents a likelihood that the corresponding condition will be satisfied within a specified time period of the input at the time step.

Other embodiments of this aspect include corresponding computer systems, apparatus, and computer programs recorded on one or more computer storage devices, each configured to perform the actions of the methods.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination.

Particular embodiments of the subject matter described in this specification can be implemented so as to realize one or more of the following advantages. A recurrent neural network can effectively be used to analyze a sequence of health events, e.g., a sequence of health events derived from an electronic medical record for a current patient. A recurrent neural network can be effectively used to predict likelihoods of events occurring within a specified time period of a most recent event in a temporal sequence, even if the events are not included in a set of possible inputs to the recurrent neural network. Recurrent neural network internal states can effectively be used to identify other temporal sequences corresponding to other patients that may include health events that are predictive of future health events that may become associated with the current patient.

A doctor or other healthcare professional can be provided with information characterizing the output of the recurrent neural network or outputs derived from outputs generated by the recurrent neural network, improving the healthcare professional's ability to provide quality healthcare to the professional's patients. For example, the healthcare professional can be provided with useful information about future health events that may become associated with a current patient, e.g., health events that are likely to be the next health event to be associated with the patient or likelihoods that certain conditions will be satisfied by events occurring within a specified time period of the most recent event in the sequence. Additionally, the healthcare professional can be provided with information that identifies the potential effect of a proposed treatment on the likelihoods of the events occurring, e.g., whether a proposed treatment may reduce or increase the likelihood of an undesirable health-related condition being satisfied for the patient in the future. Additionally, the healthcare professional can be provided with healthcare records of patients whose healthcare records were at one point in their history similar to a current patient or be provided with a summary of the health care outcomes of those patients. Additionally, in some cases, an alert can be generated for a healthcare professional that is triggered if an action the healthcare professional proposes to take causes a significant increase in risk to future predicted outcomes of that patient. Additionally, a healthcare analysis system that includes a recurrent neural network can be used to codify standard medical practice, to discover patterns in treatment and outcomes, to analyze existing medical techniques or healthcare systems, or to make novel recommendations or facilitate scientific discoveries.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification generally describes a system that can generate health analysis data from a temporal sequence that includes data identifying multiple health events using a recurrent neural network.

Figure 1:
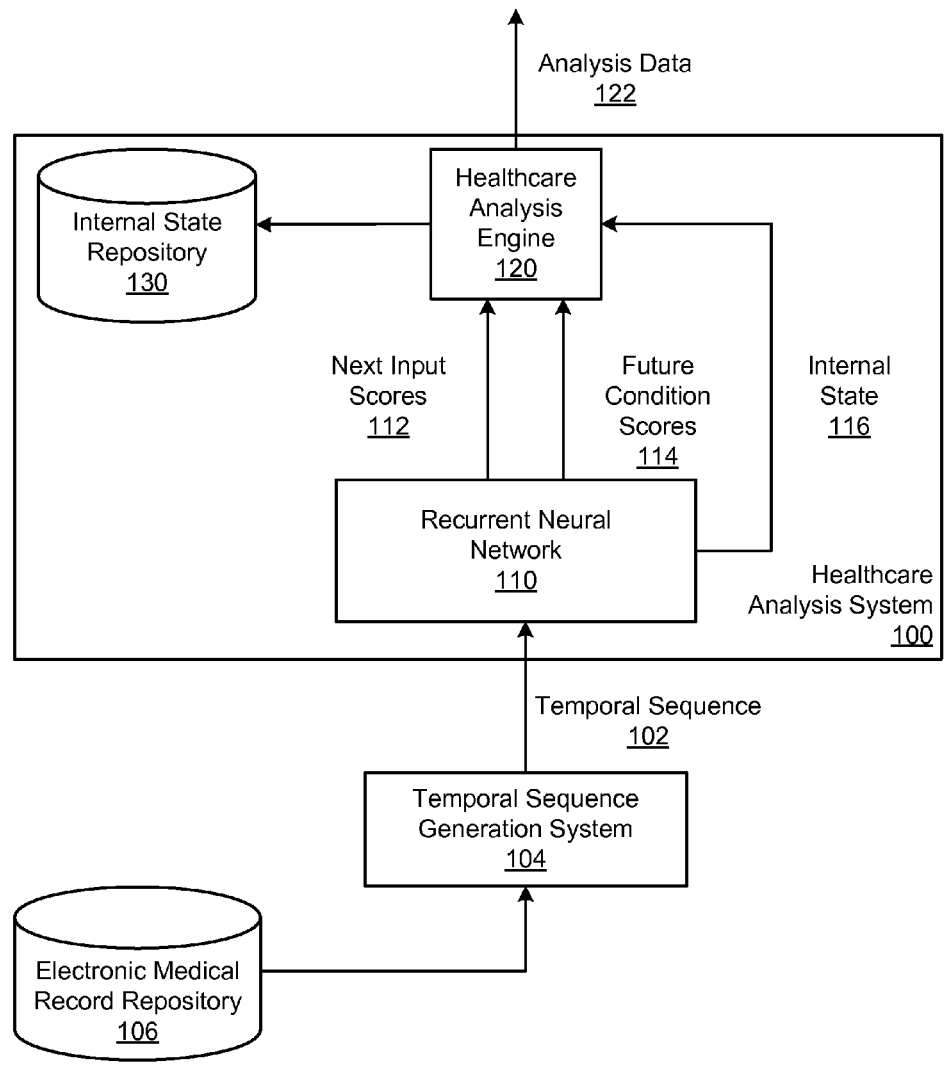
FIG. 1 shows an example healthcare analysis system.

FIG. 1 shows an example healthcare analysis system 100. The healthcare analysis system 100 is an example of a system implemented as computer programs on one or more computers in one or more locations, in which the systems, components, and techniques described below can be implemented.

The health analysis system 100 receives temporal sequences and generates health analysis data from the received temporal sequences by processing the temporal sequences using a recurrent neural network 110. For example, the healthcare analysis system 100 can receive a temporal sequence 102 and generate health analysis data 122 from the temporal sequence 102.

The temporal sequences are sequences that include health-related data, e.g., data identifying a health event, at each of multiple time steps. Each temporal sequence includes health-related data associated with a given patient, with the health events identified by the health-related data in the temporal sequence being ordered by time, so that the most-recently occurring health event is the health event at the last time step in the sequence.

In some implementations, a temporal sequence generation system 104 generates the temporal sequence 102 from an electronic medical record for a corresponding patient. An electronic medical record is an electronic collection of health information for the corresponding patient. For example, the temporal sequence generation system can obtain the electronic medical record for the patient from an electronic medical record repository 106 and generate the temporal sequence 102 from the electronic medical record by identifying health events in the electronic medal record and ordering the health events by time. In particular, the temporal sequence 102 can include a sequence of tokens at each of multiple time steps, with each token representing a health event identified in the electronic medical record. In some implementations, the temporal sequence generation system can append data identifying the time the health event occurred to the data identifying the health event in the temporal sequence 102.

Generally, the health events identified in the temporal sequences received by the healthcare analysis system 100 can include one or more of: symptoms, tests, test results, diagnoses, medications, outcomes, and so on, each of which is represented by a token from a pre-determined vocabulary of tokens. Optionally, each token is combined with data identifying the time the health event occurred in the temporal sequence. Additionally, in some cases, the temporal sequence can identify health events other than those identified by tokens from the vocabulary. For example, in some implementations, the health events in the temporal sequences may also include health-related images, e.g., X-Ray or other diagnostic images, health-related electronic documents, e.g., free-form notes generated by a doctor during an appointment, or both.

Further optionally, the health-related data can include other health-related data that may be classified as impacting the health of the patient. For example, the other data can include data characterizing a patient's activity or other health-related data collected by a patient's devices, e.g., activity tracking devices or activity tracking applications executing on mobile devices. For example, the activity data can include data identifying distances travelled by a patient on a particular day, workout or other fitness activity engaged in by the patient, meals eaten by the patient, and so on. The other health-related data can also include other data that may be considered to impact the health of the patient, e.g., prescription fulfillment data for the patient or data identifying purchases made by the patient.

The healthcare analysis system 100 processes the temporal sequence 102 using the recurrent neural network 110 to generate a network output for the temporal sequence 102. The healthcare analysis system 100 also includes a healthcare analysis engine 120 that receives the network output for the temporal sequence 102 and generates the analysis data 122 for the temporal sequence 102 from the network output.

Generally, the network output for the temporal sequence 102 includes one or more of: a set of next input scores 112, a set of future condition scores 114, or a network internal state 116 of the recurrent neural network 110.

The recurrent neural network 110 includes one or more recurrent neural network layers that generate, for each time step of a given input temporal sequence, a network internal state. In some implementations, the recurrent neural network 110 also includes an output layer, a set of logistic regression nodes, or both, that receive the network internal state and process the network internal state to generate a network output for the time step. Additionally, in some implementations, the recurrent neural network can also include one or more other kinds of neural network layers, e.g., feedforward layers, e.g., fully-connected layers, convolutional layers, pooling layers, regularization layers, and so on.

In particular, each of the recurrent neural network layers is configured to receive a layer input for the time step and compute a layer internal state for the layer for the time step. The recurrent neural network layer computes the layer internal state for the current time step from the layer internal state of the layer for the preceding time step and the layer input for the current time step in accordance with current values of a set of parameters of the layer. In some implementations, one or more of the recurrent neural network layers are configured to also use other internal states in computing the layer internal state for the time step, e.g., internal states for the layer from other previous time steps, internal states for the current time step or for previous time steps for other recurrent layers. If the current time step is the first time step in the sequence, the layer internal state for the preceding time step is an initial layer internal state, e.g., as specified by a system administrator or as generated by the healthcare analysis system 100.

If there is only one recurrent neural network layer in the recurrent neural network 110, the network internal state for a given time step is the layer internal state for the recurrent neural network layer for the time step.

If there are multiple recurrent neural network layers in the recurrent neural network 110, the layers are arranged in a sequence from a lowest layer in the sequence to a highest layer in the sequence and collectively process the health event at the time step to compute the network internal state for the time step. If there are other types of neural network layers in the recurrent neural network 100, the other neural network layers can be interspersed at various positions in the sequence, e.g., before the first recurrent layer, between two recurrent layers, after all of the recurrent layers, or some combination of these. For a given time step, the recurrent neural network 110 can provide the layer internal state from each recurrent neural network layer as the layer input for the recurrent neural network layer above the layer in the sequence. In some implementations, one or more of the recurrent neural network layers are configured to also receive inputs from one or more other layers in the sequence other than the layer below the recurrent layer.

In some implementations, one or more of the layers in the sequence can be configured to receive, at a subset of the time steps, e.g., at the first time step, or at each time step, as part of the layer input for the layer a global input, a per-record input, or both. Global inputs are inputs that are not dependent on the current temporal sequence being processed by the recurrent neural network 110. An example of a global input is data characterizing the current time of year, e.g., the current date. Per-record inputs are inputs that may be different for different temporal sequences. Examples of per-record inputs can include a genetic sequence of the patient associated with the current temporal sequence or other information characterizing the patient, e.g., demographic information for the patient.

In some implementations, if there are multiple recurrent neural network layers, the network internal state for the time step is the layer internal state of the highest layer in the sequence for the time step. In some other implementations, the healthcare analysis system 100 combines the layer internal states for the time step to generate the network internal state for the time step. For example, the healthcare analysis system 100 may compute the sum, the product, or the average of the layer internal states or may concatenate the layer internal states to generate the network internal state.

In some implementations, the recurrent neural network layers are long short-term memory (LSTM) layers. Each LSTM layer includes one or more LSTM memory blocks. Each LSTM memory block can include one or more cells that each include an input gate, a forget gate, and an output gate that allow the cell to store previous states for the cell, e.g., for use in generating a current activation or to be provided to other components of the LSTM neural network.

In implementations where the recurrent neural network 110 includes an output layer, the output layer is configured to, for each of the time steps, receive the network internal state for the time step and generate a set of next input scores for the time step. The set of next input scores for the time step includes a respective score for each health event that is represented by a token in the vocabulary of tokens. Once the recurrent neural network 110 has been trained, the next input score for a given health event represents the likelihood that the health event will be the next health event in the temporal sequence. Thus, when the recurrent neural network 110 includes an output layer, the recurrent neural network 110 is a network that has been trained to, for each time step of a given input temporal sequence, predict future health events, i.e., the health event at the next time step in the temporal sequence. The recurrent neural network 110 can be trained on training sequences using conventional machine learning training techniques, e.g., a backpropagation through time training technique.

In these implementations, the next input scores 112 for the temporal sequence 102 are the next input scores generated by the output layer for the last time step in the temporal sequence 102.

In implementations where the recurrent neural network 110 includes a set of logistic regression nodes, the set of logistic regression nodes is configured to, at each time step, receive the network internal state for the time step and to generate a set of future condition scores for the time step. The set of future condition scores includes a respective score for each condition in a pre-determined set of conditions. The score for a given condition represents a likelihood that the condition will be satisfied within a specified time period of the health event at the current time step.

The conditions can include conditions that are satisfied by the occurrence of an event, e.g., by the occurrence of a health event in represented by a token in the vocabulary. In some cases, in addition to or instead of including conditions that are satisfied by the occurrence of an event represented by a token in the vocabulary, the conditions in the predetermined set of conditions can also include conditions that are satisfied when events that are not represented by tokens in the vocabulary, i.e., are not possible health events that are included in temporal sequences processed by the recurrent neural network 110, occur within the specified time period of the health event at the current time step. Thus, while the events that can satisfy conditions in the set of predetermined conditions may overlap with the events that are represented by tokens, the set of conditions may also include conditions that are satisfied by the occurrence of other events that are not in the set.

A recurrent neural network that includes a set of logistic regression nodes is described in more detail with reference to FIGS. 7 and 8. Training the recurrent neural network to predict the likelihood of the conditions being satisfied is described in more detail below with reference to FIG. 9.

In these implementations, the condition scores 114 for the temporal sequence 102 are the future condition scores generated by the logistic regression nodes for the last time step in the temporal sequence 102.

In implementations where the network internal state 116 is included in the network output for the temporal sequence 102, the network internal state 116 for the temporal sequence 102 is the network internal state generated by the recurrent neural network 110 for the last time step in the sequence or a combination of the network internal states generated by the recurrent neural network 110 for multiple time steps in the sequence, e.g., a weighted sum, product, or a concatenation of the network internal states.

The healthcare analysis engine 120 receives the network output for the temporal sequence 122 and generates health analysis data 122 for the temporal sequence 102 and provides the health analysis data 122 for presentation to a user, e.g., to a doctor treating a patient corresponding to the temporal sequence 102. Generally, the health analysis data 122 is data that characterizes future events that may be associated with the temporal sequence 102, i.e., health events or other events that may occur after the current last health event in the temporal sequence 102.

In implementations where the neural network output for the temporal sequence 102 includes the next input scores 112, the healthcare analysis engine 120 generates health analysis data 122 that identifies health events that may occur next in the temporal sequence 102. Generating health analysis data for a temporal sequence from next input scores is described in more detail below with reference to FIG. 3.

In implementations where the neural network output for the temporal sequence 102 includes the network internal state 116, the health analysis engine 120 generates health analysis data 122 that identifies health events from other temporal sequences that are likely to be predictive of future events in the temporal sequence 102. In particular, the healthcare analysis engine 120 identifies similar internal states to the network internal state 116 from internal states stored in an internal state repository 130 and uses the similar internal states to determine the health events from other temporal sequences that are likely to be predictive of future events in the temporal sequence 102. The internal state repository 130 stores network internal states generated at various time steps in various temporal sequences and associates each network internal state with data identifying the time step and the temporal sequence for which the network internal state was generated. Generating health analysis data for a temporal sequence from a network internal state is described in more detail below with reference to FIG. 4.

In implementations where the neural network output for the temporal sequence 102 includes future condition scores 114, the health analysis engine 120 generates health analysis data 122 that characterizes the scores for the conditions. Generating health analysis data for a temporal sequence from future health condition scores is described in more detail below with reference to FIG. 5.

Figure 2:
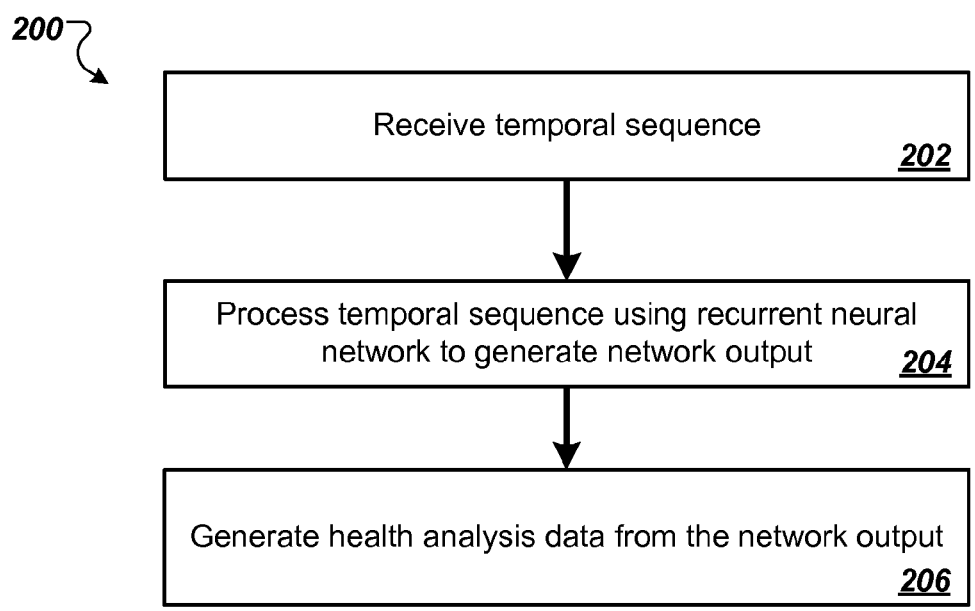
FIG. 2 is a flow diagram of an example process for generating health event data for a temporal sequence.

FIG. 2 is a flow diagram of an example process 200 for generating health event data for a temporal sequence. For convenience, the process 200 will be described as being performed by a system of one or more computers located in one or more locations. For example, a neural network training system, e.g., the healthcare analysis system 100 of FIG. 1, appropriately programmed, can perform the process 200.

The system receives an input temporal sequence (step 202). The temporal sequence includes data identifying a respective health event at each of multiple time steps. In some implementations, the temporal sequence is derived from an electronic medical record and includes data identifying a respective health event from the electronic medical record at each of multiple time steps. The health events in the sequence are ordered by time, so that the most-recently occurring health event is the health event at the last time step in the sequence.

The system processes the input temporal sequence using a recurrent neural network, e.g., the recurrent neural network 110 of FIG. 1, to generate a neural network output for the input temporal sequence (step 204).

Depending on the implementation and on the architecture of the recurrent neural network, the neural network output generated by the recurrent neural network by processing the input temporal sequence may include next input scores, future condition scores, or a network internal state.

The system generates health analysis data for the temporal sequence from the neural network output (step 206). As described above, the health analysis data is dependent on the kind of neural network output generated by the recurrent neural network.

Figure 3:
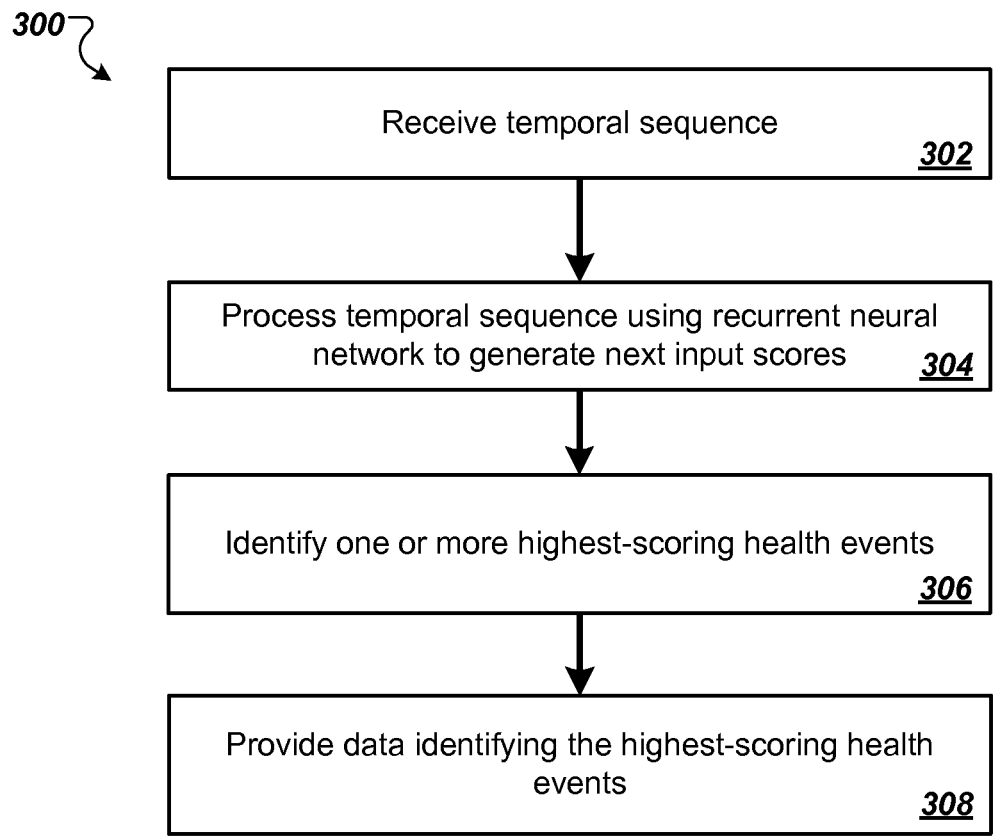
FIG. 3 is a flow diagram of an example process for generating health analysis data for a temporal sequence from next input scores.

FIG. 3 is a flow diagram of an example process 300 for generating health analysis data for a temporal sequence from next input scores. For convenience, the process 300 will be described as being performed by a system of one or more computers located in one or more locations. For example, a neural network training system, e.g., the healthcare analysis system 100 of FIG. 1, appropriately programmed, can perform the process 300.

The system receives a input temporal sequence (step 302).

The system processes the input temporal sequence using a recurrent neural network to generate next input scores for the input temporal sequence (step 304). The recurrent neural network includes one or more recurrent neural network layers and an output layer that, for each time step in the temporal sequence, is configured to receive the network internal state generated by the recurrent neural network layers for the time step and generate a set of next input scores for the time step. The set of next input scores for the time step includes a respective score for each health event that is represented by a token in the vocabulary of tokens, with the next input score for a given health event representing the likelihood that the health event will be the next health event in the temporal sequence, i.e., the health event at the next time step in the temporal sequence.

The next input scores for the input temporal sequence are the next input scores generated by the output layer for the last time step in the temporal sequence.

The system identifies one or more highest-scoring health events using the next input scores (step 306). For example, the system can select a predetermined number of health events having the highest next input scores or each health event having a next input score above a threshold value.

The system provides data identifying the highest-scoring health events and, optionally, data characterizing the next input score for each highest-scoring health event for presentation to a user (step 308). Thus, a doctor or other user may be able to view information about the health events that are likely to be the next health events to be associated with the patient corresponding to the input temporal sequence.

Figure 4:
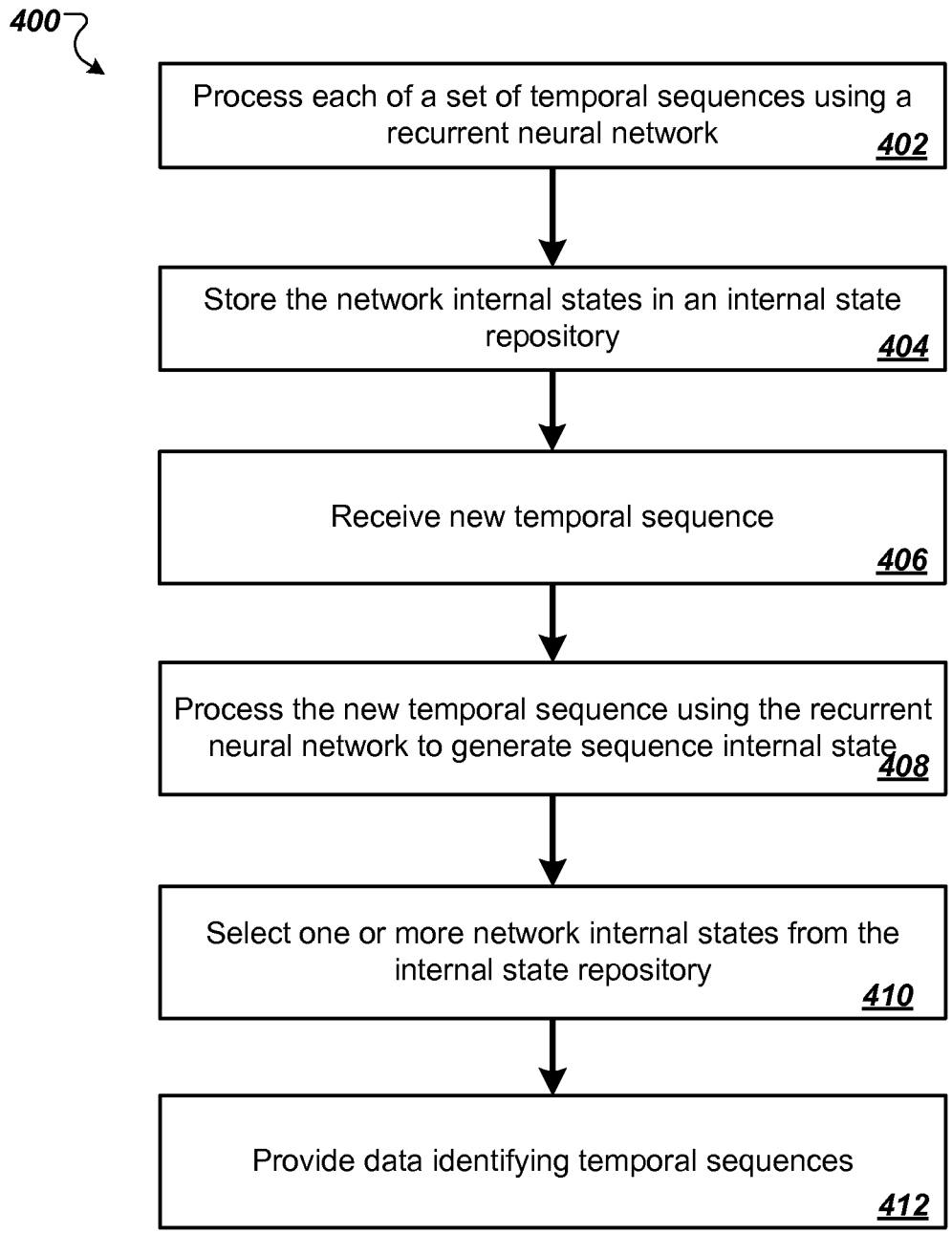
FIG. 4 is a flow diagram of an example process for generating health event data for a temporal sequence from a network internal state.

FIG. 4 is a flow diagram of an example process 400 for generating health event data for a temporal sequence from a network internal state. For convenience, the process 400 will be described as being performed by a system of one or more computers located in one or more locations. For example, a neural network training system, e.g., the neural network training system 100 of FIG. 1, appropriately programmed, can perform the process 400.

The system processes each of a set of temporal sequences using a recurrent neural network, e.g., the recurrent neural network 110, to generate a network internal state for each time step of each of the temporal sequences (step 402). Each temporal sequence in the set corresponds to a different patient, e.g., was generated from a different electronic medical record. The recurrent neural network includes one or more recurrent neural network layers and an output layer, a set of logistic regression nodes, or both. In particular, the recurrent neural network has been trained to, for each time step in a given input temporal sequence, predict future events, i.e., events occurring after the event at the current time step, from the internal state generated by the neural network for the current time step. For example, if the recurrent neural network includes an output layer, the recurrent neural network may have been trained to predict the next event in the temporal sequence, i.e., the event at the next time step after the current time step in the temporal sequence. As another example, if the recurrent neural network includes a set of logistic regression nodes, the recurrent neural network may have been trained to predict whether each of a set of events will occur within a specified time period of the event at the current time step in the temporal sequence.

The system stores the network internal states in an internal state repository and associates each network internal state with data identifying the time step and the temporal sequence for which the network internal state was generated (step 404). In some implementations, for each temporal sequence, the system stores the network internal state generated by the system for each time step in the temporal sequence in the repository. In some other implementations, the system stores only a subset of the network internal states in the repository, e.g., only the network internal states for health events preceded by at least a threshold number of other health events in the temporal sequence.

The system receives an input temporal sequence of health events (step 406).

The system processes the input temporal sequence using the recurrent neural network to determine a sequence internal state for the input temporal sequence (step 408). The sequence internal state for the input temporal sequence is the network internal state for the health event at the last time step in the sequence.

The system selects one or more network internal states from the internal state repository that are similar to the sequence internal state (step 410). The system selects the network internal states by computing a similarity measure, e.g., a cosine similarity measure, between the sequence internal state and the network internal states in the repository. For example, the system can select a predetermined number of network internal states that have the largest cosine similarity with the sequence internal state or each network internal state that has a cosine similarity with the sequence internal state that exceeds a threshold similarity. In some implementations, the system uses a different distance measure to determine similarity between internal states, e.g., Euclidian distance, Hamming distance, and so on. Similarly, the system can also regularize the internal states and then compute the distance between the regularized internal states.

The system provides data identifying the temporal sequences for which the similar network internal states were generated for presentation to a user (step 412). In particular, the system provides, for a given similar network internal state, data identifying health events in the temporal sequence for which the similar network internal state was generated that occurred subsequent to the time step for which the network internal state was generated. Because the recurrent neural network that generated both the sequence internal state and the similar network internal states was trained to predict future events from network internal states and the similar network internal states are similar to the sequence internal state, the events that occurred subsequent to the time step for which a given network internal state was generated are likely to be predictive of future events in the input temporal sequence, i.e., events that occur after the current last event in the input temporal sequence. That is, from the time step for which a given similar network internal state was generated, the corresponding patient was expected by the recurrent neural network to have a future similar to the future that the recurrent neural network expects for the current patient corresponding to the input temporal sequence. Thus, by viewing the subsequent events from network internal states, a user, e.g., a doctor, may be given an idea of the events that may follow the current last event in the input temporal sequence, i.e., future health events that may occur for the current patient.

In some other implementations, the system also provides data identifying the other health events in the temporal sequences for presentation to the user as part of the data identifying the temporal sequence for which a given network internal state was generated.

In some implementations, rather than providing the data identifying the temporal sequences for presentation to the user, the system computes statistics from the subsequent events in the temporal sequences and provides the computed statistics for presentation to the user. For example, the system may determine the portion of the temporal sequences that included a particular health event, e.g., a heart attack or a stroke, subsequent to the time step for which the similar network internal state was generated. The system may then provide data identifying the proportion for presentation the user, e.g., in the form "X % of patients expected to have similar futures as the current patient experienced the particular health event."

In some implementations, rather than storing the internal states in the internal state repository, the system can re-compute the internal states for each other temporal sequence whenever an input temporal sequence is received that is to be compared to the other temporal sequences.

Figure 5:
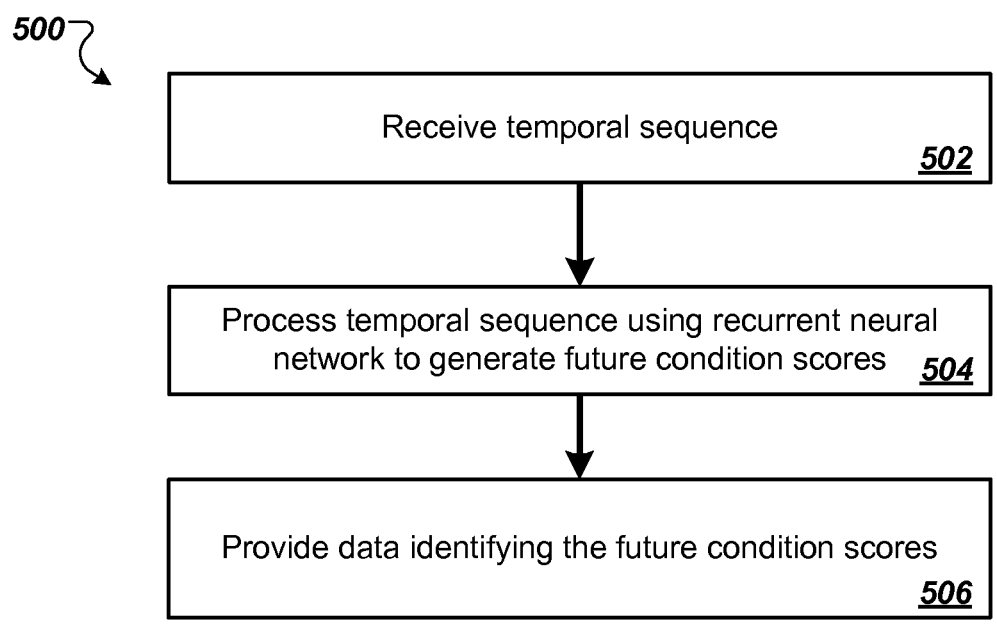
FIG. 5 is a flow diagram of an example process for generating health event data for a temporal sequence from future condition scores.

FIG. 5 is a flow diagram of an example process 500 for generating health event data for a temporal sequence from future condition scores. For convenience, the process 500 will be described as being performed by a system of one or more computers located in one or more locations. For example, a neural network training system, e.g., the neural network training system 100 of FIG. 1, appropriately programmed, can perform the process 500.

The system receives an input temporal sequence (step 502).

The system processes the input temporal sequence using a recurrent neural network, e.g., the recurrent neural network 110, to generate future condition scores for the input temporal sequence (step 504). The future condition scores include a respective future condition score for each of a predetermined set of condition. The future condition score for a given condition represents the likelihood that the condition will be satisfied within a specified time period of the event at the last time step in the input temporal sequence.

In some implementations, the recurrent neural network includes one or more recurrent neural network layers and a set of logistic regression nodes. Each logistic regression node generates, at each time step in the input temporal sequence, a future condition score for a corresponding condition from the predetermined set of conditions. A recurrent neural network that includes logistic regression nodes that generate future condition scores is described in more detail below with reference to FIGS. 7-9. In these implementations, the set of future condition scores generated by the recurrent neural network for the last time step in the input temporal sequence is the set of future condition scores for the input temporal sequence.

In some other implementations, the recurrent neural network includes an output layer that generates a set of next input scores for each time step in the input temporal sequence and does not include the logistic regression nodes. In these implementations, the system generates multiple possible temporal sequences that each include a specified number of additional time steps after the current last time step in the temporal sequences and a respective possible health event at each of the additional time steps. The system generates the multiple possible temporal sequences by performing a beam search having a specified width for each of the additional time steps. The width of the beam search defines the number of highest-scoring events that are considered by the system at each of the future time steps. The system then determines, for each of the conditions that are satisfied by the occurrence of one of the events for which future condition scores are to be generated, the proportion of possible temporal sequences that include the event that satisfies the condition at one of the additional time steps in the sequence. The system can then use the proportion as the future condition score for the corresponding condition. Optionally, the system can weight each occurrence of the event using the likelihood of occurrence of the possible temporal sequence in which the event occurred. The likelihood of occurrence of the possible temporal sequence may be, e.g., a product of the next input scores for the health events at each of the additional time steps in the sequence.

The system provides data identifying the future condition scores for presentation to a user (step 506). For example, the system can provide data identifying each condition and the future condition score for each condition or only provide data identifying one or more highest-scoring conditions for presentation to the user.

In some implementations, in addition to or instead of providing the data identifying the future condition scores for presentation to the user, the system can determine the effect of a treatment on the future condition scores and provide data identifying the effect for presentation to the user.

Figure 6:
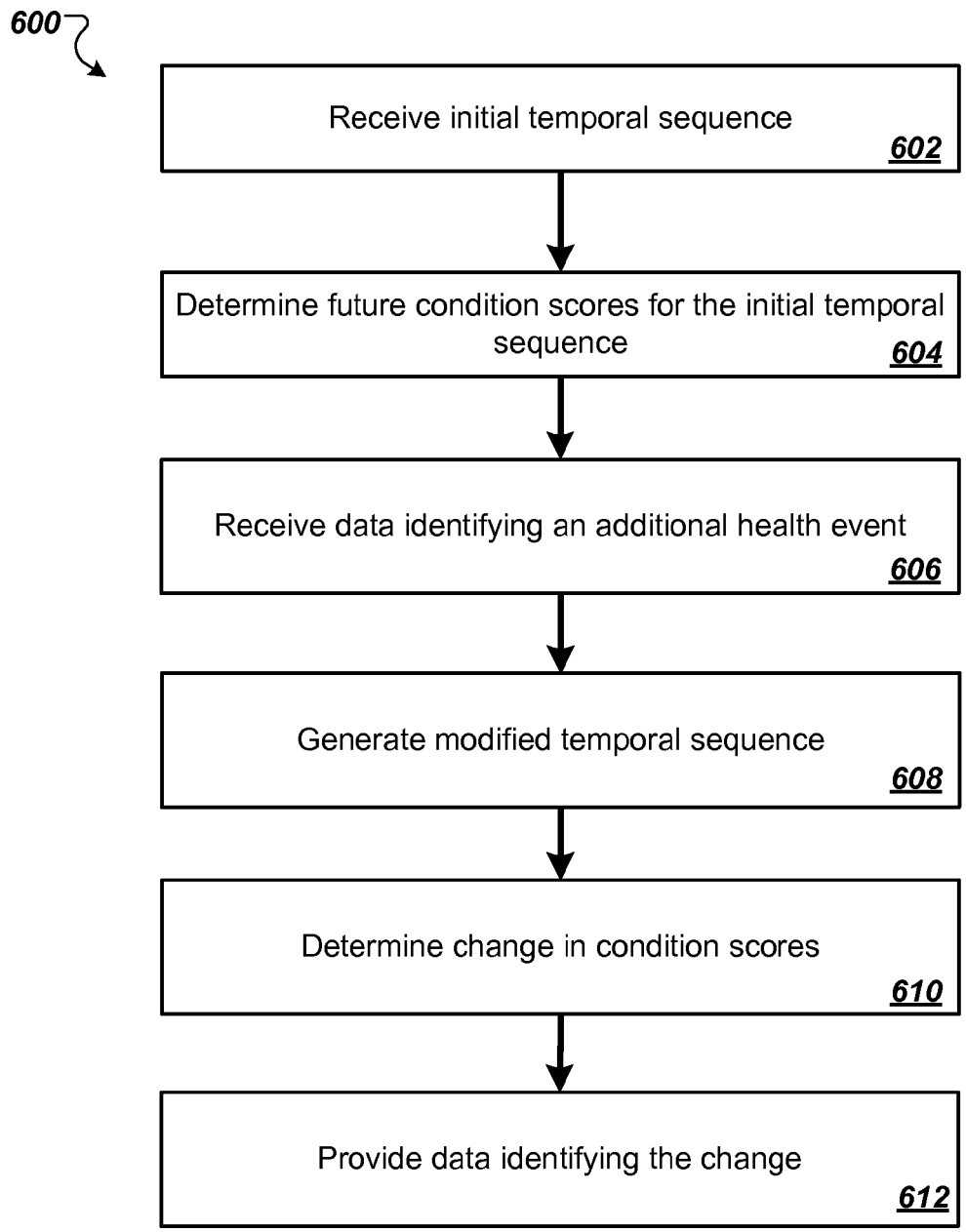
FIG. 6 is a flow diagram of an example process for determining the effect of adding an event to a temporal sequence on future condition scores.

FIG. 6 is a flow diagram of an example process 600 for determining the effect of adding an event to a temporal sequence on future condition scores. For convenience, the process 600 will be described as being performed by a system of one or more computers located in one or more locations. For example, a neural network training system, e.g., the neural network training system 100 of FIG. 1, appropriately programmed, can perform the process 600.

The system receives an initial input temporal sequence (step 602).

The system determines future condition scores for the initial input temporal sequence (step 604). For example, the system can determine future condition scores for the initial input temporal sequence as describe above with reference to FIG. 5.

The system receives data identifying an additional health event from a user (step 606). For example, the additional health event may be a potential treatment to be prescribed for a patient by a doctor.

The system generates a modified input temporal sequence by appending data identifying the additional health event, e.g., a token representing the health event, to the end of the initial input temporal sequence (step 608).

The system determines future condition scores for the modified input temporal sequence (step 610). For example, the system can determine future condition scores for the initial input temporal sequence as described above with reference to FIG. 5.

The system determines the change in the future condition scores caused by adding the additional health event to the input temporal sequence (step 612) and provides data identifying the change for presentation to the user (step 614). That is, the system computes differences between future condition scores for the modified input temporal sequence and the corresponding future condition scores for the initial input temporal sequence and provides data identifying the differences for presentation to the user. Thus, a doctor may be able to view the effect of potential treatments on the likelihood that certain conditions will be satisfied in the future.

In some implementations, the system can perform the process 600 automatically in response to a new event being added to a temporal sequence. If the new event causes the future condition score of a condition to increase by more than a threshold or to exceed a threshold, the system can generate an alert to automatically notify the user of the change. For example, a system administrator or other user may designate one or more particular conditions being satisfied as undesirable. The system can then automatically perform the process 600 in response to a new event being added to the temporal sequence and generate an alert to notify the user if the future condition score for one of the undesirable condition crosses the threshold score or increases by more than the threshold increase.

Additionally, in some implementations, the system can, in response to receiving a temporal sequence, automatically generate multiple modified temporal sequences from the temporal sequence, with each modified temporal sequence adding a different possible input health event to the temporal sequence. The possible input health events can be a subset of the health events that are represented by a token in the vocabulary, e.g., some or all of the possible treatments that are represented by tokens in the vocabulary. The system can then perform the process 600 for each of the modified temporal sequences and determine whether, for any of the modified sequences, the future condition score for one or more of the undesirable conditions decreased by more than a threshold decrease. In response to determining that, for a given modified temporal sequence, the future condition score for an undesirable condition deceased by more than the threshold decrease, the system can provide information to the user identifying the health event that was added to the temporal sequence to generate the modified temporal sequence. Thus, a doctor may be given an opportunity to consider an additional treatment that could decrease the likelihood of an undesirable condition being satisfied in the future.

Figure 7:
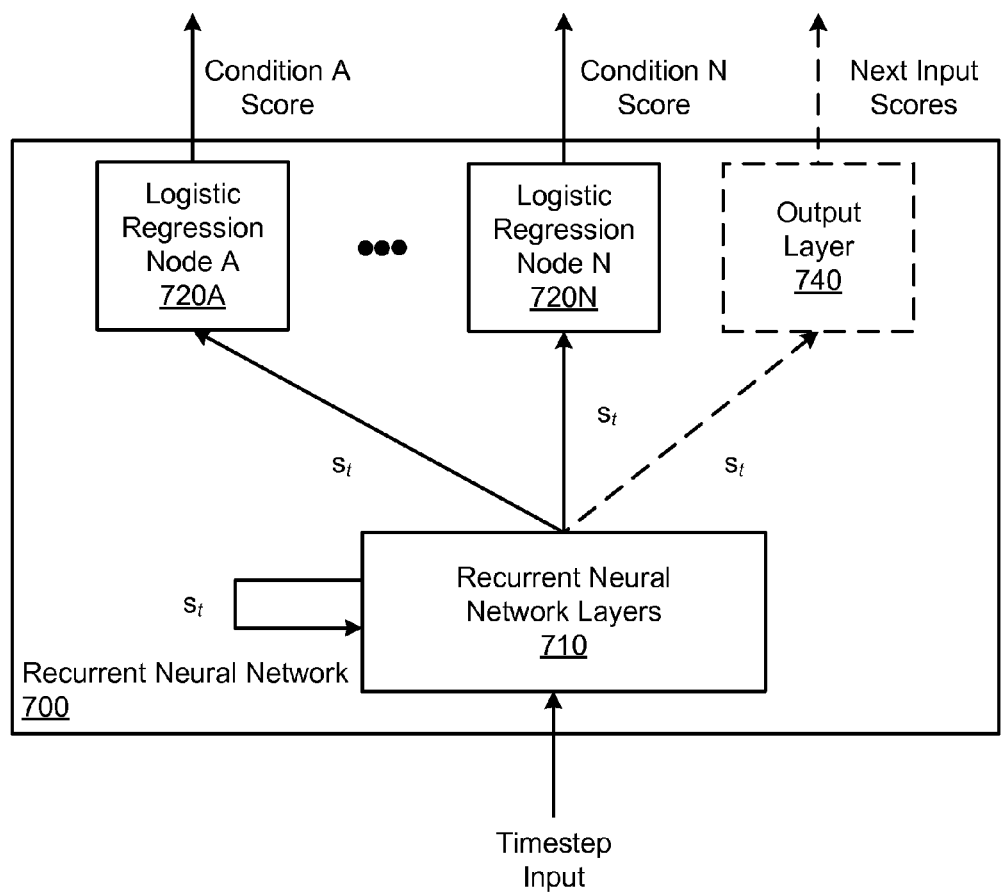
FIG. 7 shows an example recurrent neural network that is configured to generate future condition scores.

FIG. 7 shows an example recurrent neural network 700 that is configured to generate future condition scores. The recurrent neural network 700 is an example of a system implemented as computer programs on one or more computers in one or more locations, in which the systems, components, and techniques described below can be implemented.

The recurrent neural network 700 receives input sequences that include a respective input at each of multiple time steps and, for each of the time steps, generates a respective future condition score for each condition in a predetermined set of events. The future condition score for a given condition at a given time step represents the likelihood that the condition will be satisfied within a specified time period of time of the input at the time step.

The recurrent neural network 700 includes one or more recurrent neural network layers 710, multiple logistic regression nodes 720A-N, and, optionally, an output layer 740.

As described above with reference to FIG. 1, for each of the time steps, the one or more recurrent neural network layers 710 receive the input at the time step and collectively process the input to generate a network internal state for the time step.

Each of the logistic regression nodes 720A-720N corresponds to a respective condition from the predetermined set of conditions and is configured to, at each time step, receive the network internal state for the time step and process the network internal state in accordance with current values of a respective set of parameters to generate a future condition score for the corresponding event. Thus, at each time step, each of the logistic regression nodes 720A-720N generates a future condition score for a respective one of the conditions in the predetermined set of conditions.

If the recurrent neural network 700 includes an output layer 740, the output layer 740 is configured to receive the network internal state for the time step and to process the internal state to generate a respective next input score for each possible input in a set of possible inputs. The next input score for a given possible input represents the likelihood that the possible input is the next input in the input sequence, i.e., immediately follows the input at the current time step in the input sequence.

The inputs in the temporal sequence include inputs that are selected from tokens in a predetermined vocabulary that represents a set of possible input events. The conditions in the set of predetermined conditions for which the recurrent neural network 700 generates future condition scores can include conditions that are satisfied by the occurrence of events that are not represented by tokens in the predetermined vocabulary, i.e., are not possible input events that may be included in temporal sequences processed by the recurrent neural network 700, events that are represented by tokens, or both. Thus, while the events in the set of events that satisfy any of the conditions in the predetermined set of conditions for which the recurrent neural network 700 generates future condition scores may overlap with the events that are represented by tokens, the set of events may also include other events that are not in the set.

Figure 8:
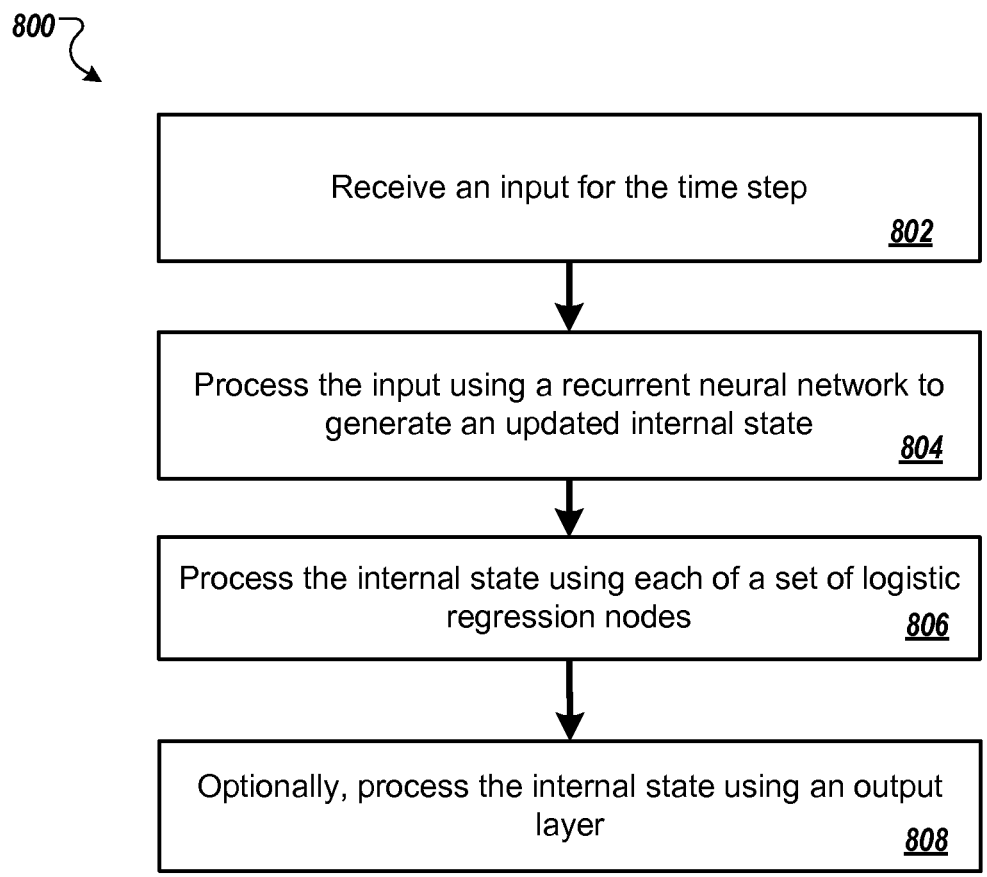
FIG. 8 is a flow diagram of an example process for generating future condition scores for a given time step.

FIG. 8 is a flow diagram of an example process 800 for generating future condition scores for a given time step. For convenience, the process 800 will be described as being performed by a system of one or more computers located in one or more locations. For example, a recurrent neural network, e.g., the recurrent neural network 700 of FIG. 7, appropriately programmed, can perform the process 300.

The system receives an input for the time step, e.g., a token representing a health event (step 802).

The system processes the input using one or more recurrent neural network layers, e.g., the recurrent neural network layers 710 of FIG. 7, to generate a network internal state for the recurrent neural network for the time step (step 804). The one or more neural network layers generate the network internal state, e.g., as described above with reference to FIG. 1.

The system processes the network internal state using each of a set of logistic regression nodes, e.g., the logistic regression nodes 720A-720N of FIG. 7, to generate a set of future condition scores (step 806). Each of the logistic regression nodes corresponds to a respective condition from a predetermined set of conditions and generates a future condition score for the corresponding condition by processing the internal state in accordance with current values of a set of parameters of the logistic regression node.

Optionally, the system also processes the network internal state using an output layer, e.g., the output layer 740 of FIG. 7, to generate a respective next input score for each of a set of possible inputs (step 808). The output layer generates the respective next input scores by processing the network internal state in accordance with current values of a set of output layer parameters.

The process 800 can be performed for a neural network input for which the desired output, i.e., the neural network output that should be generated by the system for the input, is not known. The system can also perform the process 800 on inputs in a set of training sequences, i.e., a set of inputs for which the output that should be predicted by the system is known, in order to train the system, i.e., to determine trained values for the parameters of the recurrent neural network layers, the logistic regression nodes, and, in some implementations, the output layer. In particular, the process 800 can be performed repeatedly on inputs from a set of training sequences as part of a machine learning training technique to train the neural network, e.g., a back-propagation through time training technique. An example training process is described in more detail below with reference to FIG. 9.

Figure 9:
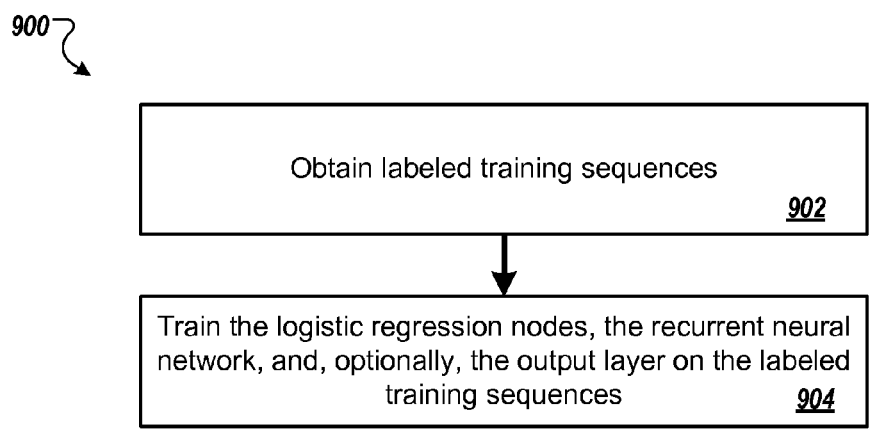
FIG. 9 is a flow diagram of an example process for training a recurrent neural network to generate future condition scores.

FIG. 9 is a flow diagram of an example process 900 for training a recurrent neural network to generate future condition scores. For convenience, the process 900 will be described as being performed by a system of one or more computers located in one or more locations. For example, a recurrent neural network, e.g., the recurrent neural network 700 of FIG. 7, appropriately programmed, can perform the process 700.

The system obtains labeled training sequences (step 502). Each of the obtained training sequences is a sequence of inputs at each of multiple time steps. Each training sequence also includes, at each of the time steps, a respective indicator variable for each of the conditions in the predetermined set of conditions for which the recurrent neural network generates future condition scores. The indicator variable for a given condition at a given time step indicates whether or not the condition was satisfied within the specified period of time from the input at the time step. For example, the indicator variable may have a value of one if the condition was satisfied and a value of zero if the condition was not satisfied. Thus, at each time step, the labeled training sequence includes an input and a respective indicator variable for each of the conditions in the predetermined set of conditions.

In some implementations, the system receives training sequences that have already been labeled with the indicator variables. In some other implementations, the system generates the labeled training sequences by computing the indicator variables for each of the conditions at each of the time steps. For example, the system can, for a given input at a given time step of a training sequence, determine when the input occurred and access data identifying occurrences of events that satisfy the conditions in the predetermined set of conditions. The system can then determine, for each of the conditions, whether the condition was satisfied within the specified time period of when the input at the time step occurred and set the value of the indicator variable for the event accordingly.

The system trains the one or more recurrent neural network layers, the logistic regression nodes, and, optionally, the output layer on the labeled training sequences (step 504). In particular, the system determines trained values of the parameters of the recurrent neural network layers, the logistic regression nodes, and the output layers from initial values of the parameters by performing multiple iterations of a machine learning training technique. As part of the training technique, the system minimizes or maximizes an objective function. If the system includes only logistic regression nodes and not an output layer, the objective function depends on, for a given time step in a given training sequence, an error between the future condition scores generated by the logistic regression nodes for the time step and the indicator variables for the corresponding conditions at the time step. If the system also includes an output layer, the objective function also depends on, for the time step, an error between the next input scores generated by the output layer for the time step and the input at the next time step in the training sequence.

As described above, the recurrent neural network 700 can process temporal sequences that include data identifying health events associated with a patient to generate future condition scores. However, the recurrent neural network 700 can be trained to generate future condition scores for temporal sequences that include data identifying any type of temporal event, i.e., any temporal sequences that include data identifying events that are ordered by when those events occurred over time.

For example, the recurrent neural network 700 can be trained to generate future condition scores for temporal sequences that include data identifying transactions found in financial statements of a user, e.g., bank transactions that might appear on a bank statement, credit card transactions that might appear on credit card statements, and so on. The future condition scores in this context may include scores for conditions that are satisfied by various types of financial transactions being made, scores for conditions that are satisfied by events occurring that aren't financial transactions of the kind that appear in financial statements, e.g., a tax audit, or both.

As another example, the recurrent neural network 700 can be trained to generate future condition scores for temporal sequences that include data identifying stock market transactions. In this context, temporal sequences can either include stock purchases and sales by a single entity or by all entities participating in the stock market.

As another example, the recurrent neural network 700 can be trained to generate future condition scores for temporal sequences that include data identifying maintenance records for machinery or electronics, e.g., for airplanes, vehicles, data center components, and so on. The future condition scores in this context may include scores for conditions that are satisfied by various types of maintenance-related events as well as scores for conditions that are satisfied by the occurrence of events that don't typically appear in maintenance records, e.g., an in-flight failure for airplanes.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A recurrent neural network system configured to process a temporal sequence comprising a respective input at each of a plurality of time steps, the recurrent neural network system comprising:
   one or more recurrent neural network layers, wherein the one or more recurrent neural network layers are configured to, for each of the plurality of time steps:
      receive the input at the time step; and
      collectively process the input at the time step to generate a network internal state for the time step;
   one or more logistic regression nodes, wherein each of the logistic regression nodes corresponds to a respective condition from a predetermined set of conditions, and wherein each of the logistic regression nodes is configured to, for each of the plurality of time steps:
      receive the network internal state for the time step; and
      process the network internal state for the time step in accordance with current values of a set of parameters of the logistic regression node to generate a future condition score for the corresponding condition for the time step, wherein the future condition score for the corresponding condition represents a likelihood that the corresponding condition will be satisfied within a specified time period of the input at the time step.

2. The recurrent neural network system of claim 1, further comprising:
   an output layer, wherein the output layer is configured to, for each of the plurality of time steps:
      receive the network internal state for the time step; and
      process the network internal state for the time step in accordance with current values of a set of parameters of the output layer to generate a respective next input score for each of a plurality of possible next inputs, wherein the respective next input score for each of the plurality of possible next inputs represents a likelihood that the possible next input will be an input at a next time step in the temporal sequence.

3. The recurrent neural network system of claim 1, wherein each of the one or more recurrent neural network layers is configured to, for each of the plurality of time steps:
   receive a layer input for the time step; and
   process the layer input for the time step and a layer internal state for the recurrent neural network layer for a preceding time step in accordance with a current values of a set of parameters for the recurrent neural network layer to generate a layer internal sate for the recurrent neural network layer for the time step.

4. The recurrent neural network system of claim 3, wherein the recurrent neural network system includes only one recurrent neural network layer, and wherein the layer internal state for the recurrent neural network layer for the time step is the network internal state for the time step.

5. The recurrent neural network system of claim 3, wherein the recurrent neural network system includes a plurality of recurrent neural network layers arranged in a sequence, and wherein the network internal state for the time step is a layer internal state of a highest recurrent neural network layer in the sequence for the time step.

6. The recurrent neural network system of claim 3, wherein the recurrent neural network system includes a plurality of recurrent neural network layers, and wherein the network internal state for the time step is combination of the layer internal states of the recurrent neural network layers for the time step.

7. The recurrent neural network system of claim 1, wherein each input in the temporal sequence is selected from a set of possible inputs to the recurrent neural network system.

8. The recurrent neural network system of claim 7, wherein the predetermined set of conditions includes conditions that are satisfied when events that are not in the set of possible inputs to the recurrent neural network system occur within a specified time period of the input at the time step.

9. The recurrent neural network system of claim 1, wherein each of the inputs at the plurality of time steps is health-related data associated with a patient, and wherein the conditions in the predetermined set of conditions are conditions that are satisfied when a health-related event occurs in association with the patient.

10. A method for processing a temporal sequence comprising a respective input at each of a plurality of time steps using a recurrent neural network system comprising one or more recurrent neural network layers and one or more logistic regression nodes, the method comprising, for each of the plurality of time steps:
   receiving the input at the time step;
   processing the input at the time step through the one or more recurrent neural network layers to generate a network internal state for the time step; and
   processing the network internal state using each of the one or more logistic regression nodes, wherein each of the logistic regression nodes corresponds to a respective condition from a predetermined set of conditions, and wherein processing the network internal state using each of the one or more logistic regression nodes comprises:
processing the network internal state for the time step using the logistic regression node in accordance with current values of a set of parameters of the logistic regression node to generate a future condition score for the corresponding condition for the time step, wherein the future condition score for the corresponding condition represents a likelihood that the corresponding condition will be satisfied within a specified time period of the input at the time step.

11. The method of claim 10, wherein the recurrent neural network system further comprises an output layer, and wherein the method further comprises, for each of the plurality of time steps:
processing the network internal state for the time step using the output layer in accordance with current values of a set of parameters of the output layer to generate a respective next input score for each of a plurality of possible next inputs, wherein the respective next input score for each of the plurality of possible next inputs represents a likelihood that the possible next input will be an input at a next time step in the temporal sequence.

12. The method of claim 10, wherein each of the one or more recurrent neural network layers is configured to, for each of the plurality of time steps:
receive a layer input for the time step; and
process the layer input for the time step and a layer internal state for the recurrent neural network layer for a preceding time step in accordance with a current values of a set of parameters for the recurrent neural network layer to generate a layer internal state for the recurrent neural network layer for the time step.

13. The method of claim 12, wherein the recurrent neural network system includes only one recurrent neural network layer, and wherein the layer internal state for the recurrent neural network layer for the time step is the network internal state for the time step.

14. The method of claim 12, wherein the recurrent neural network system includes a plurality of recurrent neural network layers arranged in a sequence, and wherein the network internal state for the time step is a layer internal state of a highest recurrent neural network layer in the sequence for the time step.

15. The method of claim 12, wherein the recurrent neural network system includes a plurality of recurrent neural network layers, and wherein the network internal state for the time step is combination of the layer internal states of the recurrent neural network layers for the time step.

16. The method of claim 10, wherein each input in the temporal sequence is selected from a set of possible inputs to the recurrent neural network system.

17. The method of claim 16, wherein the predetermined set of conditions includes conditions that are satisfied when events that are not in the set of possible inputs to the recurrent neural network system occur within a specified time period of the input at the time step.

18. The method of claim 10, wherein each of the inputs at the plurality of time steps is health-related data associated with a patient, and wherein one or more of the conditions in the predetermined set of conditions are conditions that are satisfied when a health-related event occurs in association with the patient.

19. A computer program product encoded on one or more non-transitory computer readable media, the computer program product comprising instructions that when executed by one or more computers cause the one or more computers to perform operations for processing a temporal sequence comprising a respective input at each of a plurality of time steps using a recurrent neural network system comprising one or more recurrent neural network layers and one or more logistic regression nodes, the operations comprising, for each of the plurality of time steps:
receiving the input at the time step;
processing the input at the time step through the one or more recurrent neural network layers to generate a network internal state for the time step; and
processing the network internal state using each of the one or more logistic regression nodes, wherein each of the logistic regression nodes corresponds to a respective condition from a predetermined set of conditions, and wherein processing the network internal state using each of the one or more logistic regression nodes comprises:
processing the network internal state for the time step using the logistic regression node in accordance with current values of a set of parameters of the logistic regression node to generate a future condition score for the corresponding condition for the time step, wherein the future condition score for the corresponding condition represents a likelihood that the corresponding condition will be satisfied within a specified time period of the input at the time step.

20. The computer program product of claim 19, wherein the recurrent neural network system further comprises an output layer, and wherein the operations further comprise, for each of the plurality of time steps:
processing the network internal state for the time step using the output layer in accordance with current values of a set of parameters of the output layer to generate a respective next input score for each of a plurality of possible next inputs, wherein the respective next input score for each of the plurality of possible next inputs represents a likelihood that the possible next input will be an input at a next time step in the temporal sequence.

* * * * *